(12) United States Patent
Michael et al.

(10) Patent No.: US 7,018,381 B2
(45) Date of Patent: Mar. 28, 2006

(54) APPARATUS FOR REMOVING AN OSTEOPHYTE (75) Inventors: Jeff Michael, Warsaw, IN (US); Rodney Bays, Pierceton, IN (US); Jamie Hanneken, North Manchester, IN (US); Michael Daniels, Warsaw, IN (US); Robert Hodorek, Warsaw, IN (US); Scott Steffensmeier, Warsaw, IN (US); Lynn Kirkpatrick, Columbia City, IN (US); Linggawati Tanamal, Fort Wayne, IN (US)

(73) Assignee: Zimmer Technology, Inc., Chicago, IL (US)

( * ) Notice: Subject to any disclaimer, the term of this patent is extended or adjusted under 35 U.S.C. 154(b) by 134 days.

(21) Appl. No.: 10/274,337

(22) Filed: Oct. 18, 2002

(65) Prior Publication Data

US 2004/0078041 A1 Apr. 22, 2004

(51) Int. Cl.
*A61B 17/00* (2006.01)

(52) U.S. Cl. .......................................... 606/80; 606/84

(58) Field of Classification Search .................. 606/80, 606/85, 170, 171, 172, 84, 89, 82, 88, 104
See application file for complete search history.

(56) References Cited

U.S. PATENT DOCUMENTS

| 505,818 | A | * | 10/1893 | Dallas | 606/85 |
|---|---|---|---|---|---|
| 3,986,512 | A | | 10/1976 | Walliser | |
| 4,625,725 | A | * | 12/1986 | Davison et al. | 606/85 |
| 4,872,452 | A | * | 10/1989 | Alexson | 606/85 |
| 5,027,519 | A | * | 7/1991 | De Vincentis | 30/494 |
| 5,387,215 | A | * | 2/1995 | Fisher | 606/79 |
| 5,716,362 | A | * | 2/1998 | Treacy | 606/87 |
| 5,913,858 | A | * | 6/1999 | Calandruccio et al. | 606/79 |
| 6,015,419 | A | * | 1/2000 | Strome et al. | 606/167 |
| 6,214,006 | B1 | * | 4/2001 | Metz-Stavenhagen | 606/61 |
| 6,214,009 | B1 | * | 4/2001 | Toriumi et al. | 606/80 |
| 6,368,324 | B1 | | 4/2002 | Dinger et al. | |
| 6,451,022 | B1 | | 9/2002 | Dinger et al. | |
| 6,485,495 | B1 | | 11/2002 | Jenkinson | |
| 6,537,280 | B1 | | 3/2003 | Dinger et al. | |
| 6,595,996 | B1 | | 7/2003 | Dinger et al. | |
| 6,610,066 | B1 | * | 8/2003 | Dinger et al. | 606/85 |
| 6,635,060 | B1 | * | 10/2003 | Hanson et al. | 606/79 |

* cited by examiner

*Primary Examiner*—Pedro Philogene
(74) *Attorney, Agent, or Firm*—Cary R. Reeves; Jonathan Feuchtwang (57) ABSTRACT An apparatus for removing an osteophyte includes an elongated member. A portion of the elongated member includes a blunt end. A burr extends from this portion at a location proximal to the blunt end. An alternative embodiment includes a generally tongue-shaped elongated member. The elongated member includes a first portion and a second portion that define a passageway. The second portion includes a blunt end. At least one of a post and a wall extend from the first portion. A burr is coupled the second portion and the passageway at a location proximal to the blunt end. The burr includes a base with a generally pie-slice shaped perimeter, and includes a generally convex surface extending from the base. The generally convex surface includes a smooth portion facing generally toward the blunt end and a perforated, non-smooth portion facing generally toward the first portion of the elongated member.

53 Claims, 7 Drawing Sheets

APPARATUS FOR REMOVING AN OSTEOPHYTE

FIELD OF THE INVENTION

The present invention relates generally to the field of orthopaedics, and, more particularly, to an apparatus for removing an osteophyte.

BACKGROUND

An osteophyte (sometimes called a "bone spur") is a projection that can form on a bone of a joint when an animal's body attempts to better distribute weight across a surface that has been damaged by arthritis or other conditions. Osteophytes can limit joint motion and contribute to joint pain, and they can become increasingly more restrictive and painful as they grow. Historical approaches to the removal of osteophytes from hard to reach areas have required difficult contortions of affected joints and tedious manipulations of cutting tools.

Figure 1:
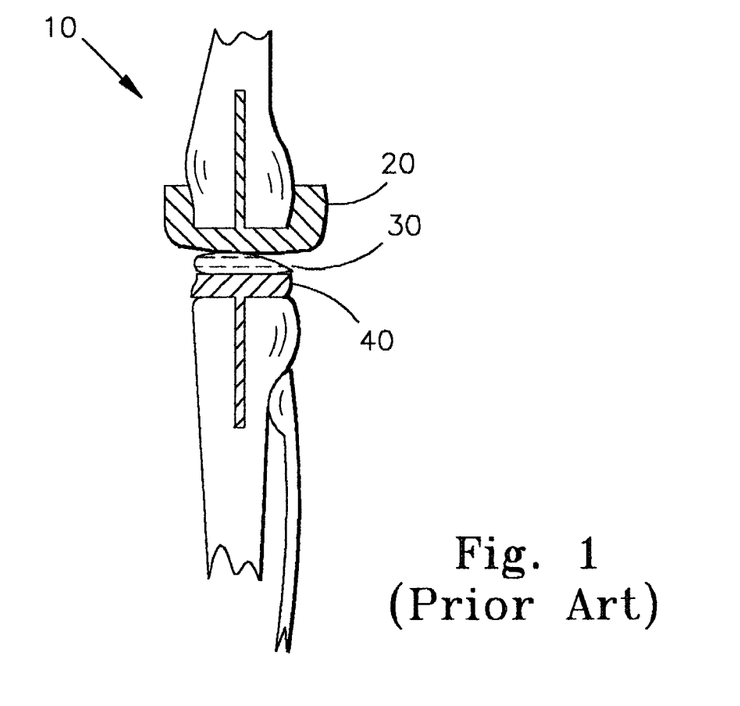
FIG. 1 (prior art) shows a lateral view of a simplified prosthetic knee.
Figure 2:
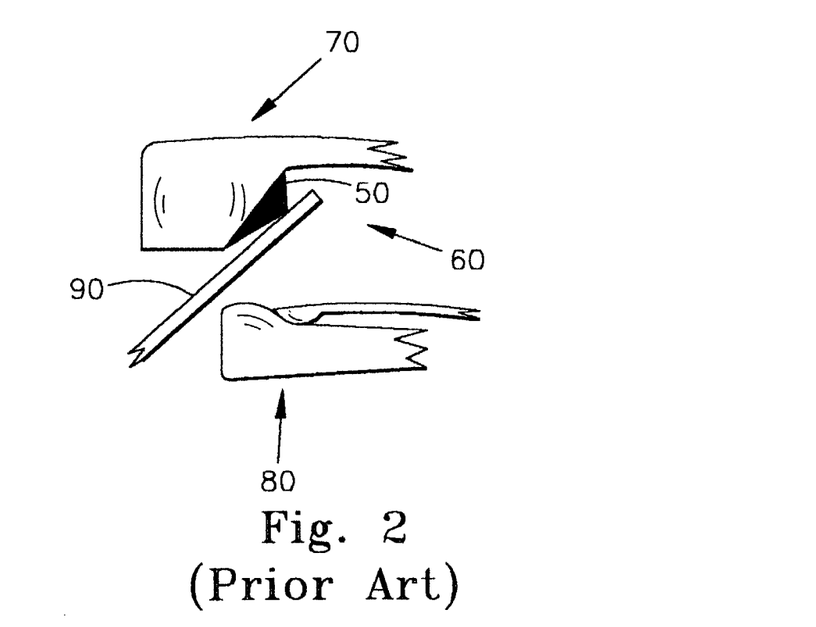
FIG. 2 (prior art) shows a historical removal of one or more osteophytes from a posterior condylar region in preparation of a distal femur for receiving the distal femoral component of FIG. 1.

For example, FIG. 1 (prior art) shows a lateral view of a simplified prosthetic knee 10 (including a distal femoral component 20, a meniscial component 30, and a proximal tibial component 40) and FIG. 2 (prior art) shows a historical removal of an osteophyte 50 from a posterior condylar region 60 in preparation of a distal femur 70 for receiving the distal femoral component 20 of FIG. 1. After end portions of the distal femur 70 and a proximal tibia 80 have been removed and the remaining surfaces have been planed or otherwise reshaped to receive the prosthesis, the historical approach has required hyperflexion of the knee joint to gain access to the osteophyte 50 with a cutting tool 90, followed by manual reciprocation of the cutting tool 90 to remove the osteophyte 50. The extreme flexions of the knee joints have been difficult to achieve for patients with large thighs and/or other physical limitations, and the manual operations of the cutting tools have been tedious and time consuming.

SUMMARY OF THE INVENTION

The present invention provides an apparatus for removing an osteophyte. In one embodiment, the apparatus includes an elongated member. The elongated member includes a first portion and a second portion. The second portion includes a blunt end. A burr extends from the second portion at a location proximal to the blunt end.

In an alternative embodiment, the apparatus includes a means for removing the osteophyte from a bone and a means, coupled to the removing means, for positioning the removing means relative to at least a first surface of the bone.

In another alternative embodiment, the apparatus includes a generally tongue-shaped elongated member. The elongated member includes a first portion and a second portion. The first portion and the second portion define a passageway. The second portion includes a blunt end. At least one of a post and a wall extend from the first portion. A burr is coupled the second portion and the passageway at a location proximal to the blunt end. The burr includes a base with a generally pie-slice shaped perimeter, and further includes a generally convex surface extending from the base. The generally convex surface includes a smooth portion facing generally toward the blunt end and a perforated, non-smooth portion facing generally toward the first portion of the elongated member.

The above-noted features and advantages of the present invention, as well as additional features and advantages, will be readily apparent to those skilled in the art upon reference to the following detailed description and the accompanying drawings.

DETAILED DESCRIPTION OF EXEMPLARY EMBODIMENT(S)

Figure 3:
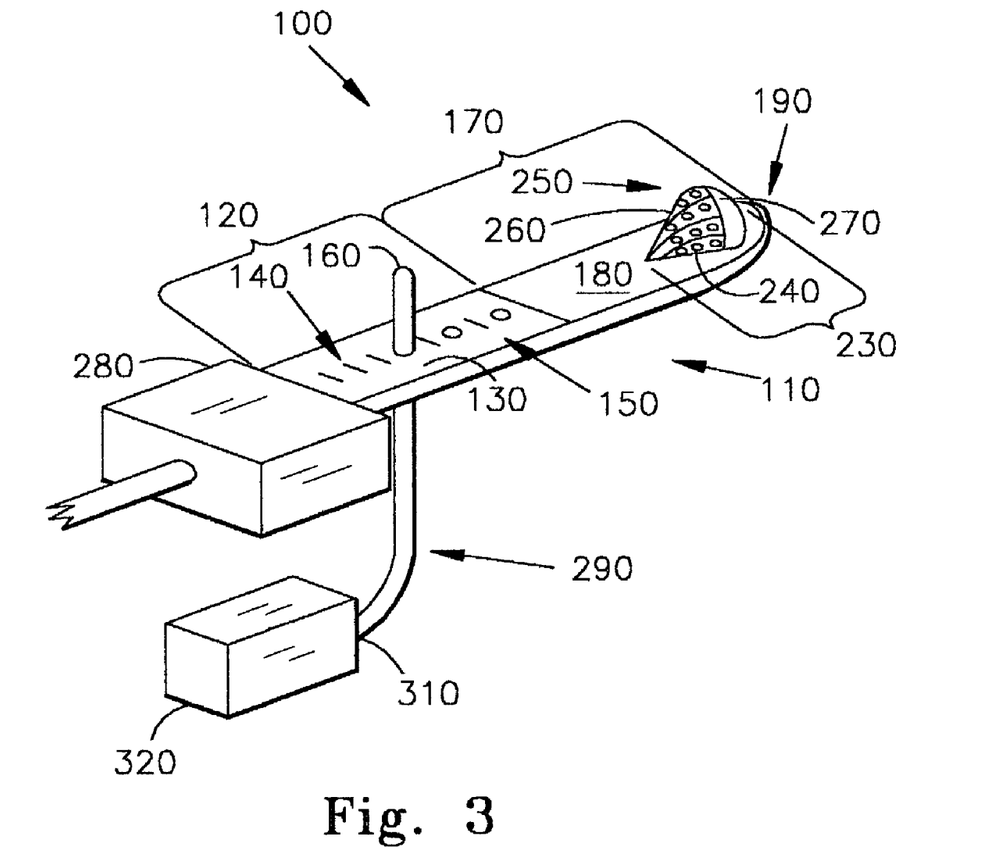
FIG. 3 shows a perspective view of an exemplary apparatus for removing an osteophyte according to the present invention.

FIG. 3 shows a perspective view of an exemplary apparatus for removing an osteophyte 100 according to the present invention. The apparatus 100 includes an elongated member 110 made from stainless steel, plastic, or any other material suitable for use in surgical procedures. In the apparatus 100, the elongated member 110 is reusable, and accordingly, is made suitable for sterilization in an autoclave. In alternative embodiments the elongated member 110 may be disposable. Further, in the apparatus 100, the elongated member 110 is generally tongue-shaped or surfboard-shaped. However, it should be appreciated that in alternative embodiments the elongated member 110 may be narrower, wider, may include additional curvatures, angles and/or contours, or may be configured in any other suitable manner.

The elongated member 110 includes a first portion 120. The first portion 120 includes a generally planar surface 130 with a longitudinally spaced series of cylindrical recesses or cavities 140 therein and a longitudinally oriented series of transverse markings or graduations 150 thereon. A stop member 160 is removably fitted into one of the cavities 140 and extends away from the surface 130. In general, the stop member 160 is configured and positioned to limit an insertion of the elongated member 110 into a patient's body as discussed in further detail below. The stop member 160 is made from stainless steel, plastic, or any other material suitable for use in surgical procedures. In the apparatus 100, the stop member 160 is reusable, and accordingly, is made suitable for sterilization in an autoclave. In alternative embodiments the stop member 160 may be disposable. Further, in the apparatus 100 the stop member 160 is implemented as a peg or post. However, in alternative embodiments the stop member 160 may include a transverse wall (see FIG. 7) or any other suitable component or components.

The elongated member 110 also includes a second portion 170. The second portion 170 includes a generally planar, smooth surface 180 and a blunt end 190. Additionally, the first portion 120 and second portion 170 of the elongated member 110 define a tunnel or passageway 200 within the elongated member 110 having a first end 210 in the first portion 120 and a second end 220 in the second portion 170 (not visible in FIG. 3; but see FIG. 5 and FIG. 6).

A generally convex rasp or burr 230 extends from the second portion 170 of the elongated member 110 proximal to the blunt end 190. The burr 230 is positioned over the second end 220 of the passageway 200 such that it is pneumatically coupled thereto (see FIG. 5 and FIG. 6). The burr 230 is made from stainless steel, plastic, or any other material suitable for use in surgical procedures. In the apparatus 100, the burr 230 is reusable, and accordingly, is made for sterilization in an autoclave. In alternative embodiments, the burr 230 may be disposable. The burr 230 includes a base 240 with a generally pie-slice shaped perimeter (not completely visible in FIG. 3; but see also FIG. 4) that is fastened to the second portion 170 of the elongated member 110 by welding, gluing, compression fitting, a threaded interface, or in any other manner. It should be appreciated that in alternative embodiments the burr 230 may be removable and/or its base 240 may be of any other suitable shape. Further, the burr 230 includes a generally convex surface 250 that extends from its base 240. The generally convex surface 250 includes a perforated, non-smooth portion 260 that faces generally toward the first portion 120 of the elongated member 110. The perforations of the non-smooth portion 260 are implemented as holes, slits, a combination thereof, or any other openings suitable for removing bits or fragments of an osteophyte during operation. In the apparatus 100, the non-smooth portion 260 has diamond dust or fragments generally around and between the perforations. In alternative embodiments, the non-smooth portion 260 may include any other abrasives, serrations, studs, edges, or the like that are suitable for removing osteophytes. The generally convex surface 250 also includes a smooth portion 270 that faces generally toward the blunt end 190.

A drive device 280 is attached to the first portion 120 of the elongated member 110. In general, the drive device 280 is automated to move the elongated member 110 (and thus, the burr 230) as discussed in further detail below. Accordingly, the drive device 280 is an oscillating saw driver from Stryker Instruments (a division of Stryker Corporation) of Kalamazoo, Mich., or any other suitable device. To this end, it should be appreciated that in the apparatus 100, the first portion 120 of the elongated member 110 is suitably configured to attach to the drive device 280 in manner similar to that of an oscillating saw blade.

Figure 5:
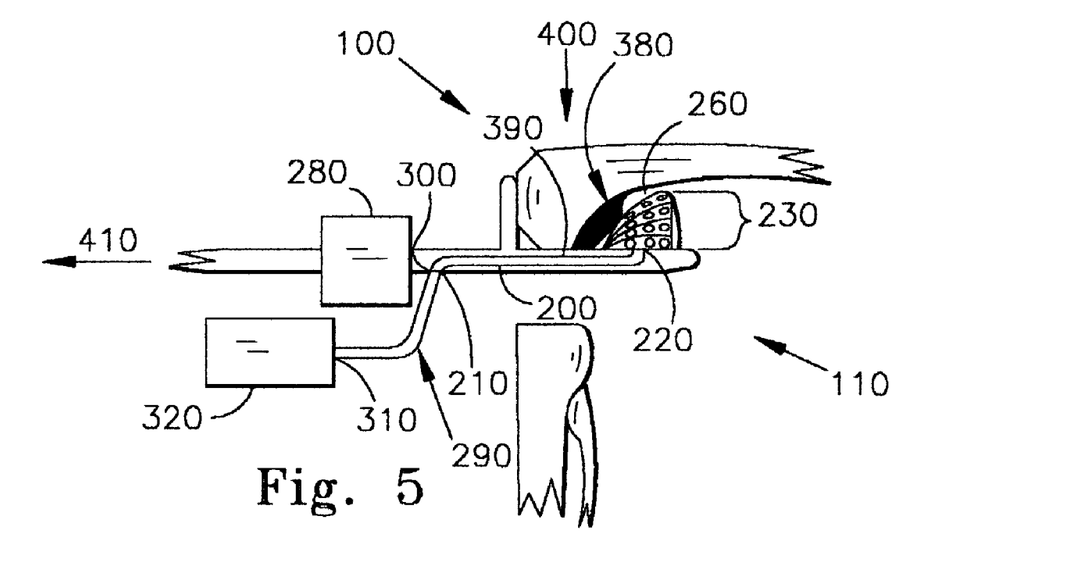
FIG. 5 shows a lateral cross-sectional view of the apparatus of FIG. 3 prior to an exemplary removal of a posterior condylar osteophyte from a knee joint.
Figure 6:
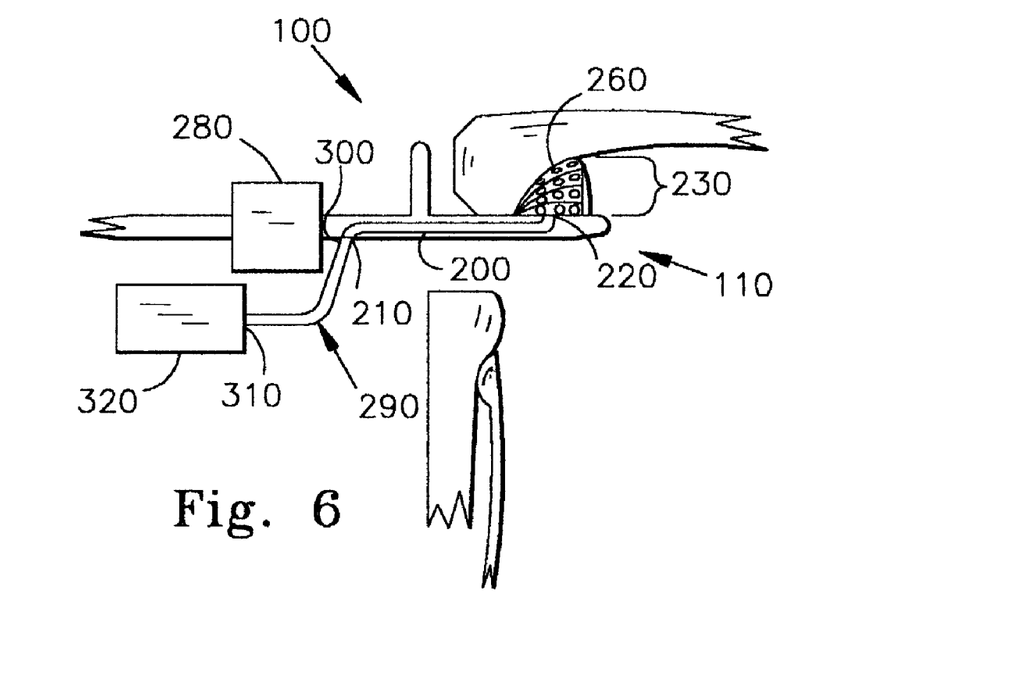
FIG. 6 shows a lateral cross-sectional view of the apparatus of FIG. 3 after removal of the osteophyte of FIG. 5.

A suction tube or hose 290 includes a first end 300 attached to the first end 210 of the passageway 200, and further includes a second end 310 attached to a suction device 320 (not all visible in FIG. 3; but see also FIG. 5 and FIG. 6). The hose 290 and the suction device 320 are suitably configured to carry away bits or fragments of an osteophyte during operation.

Figure 4:
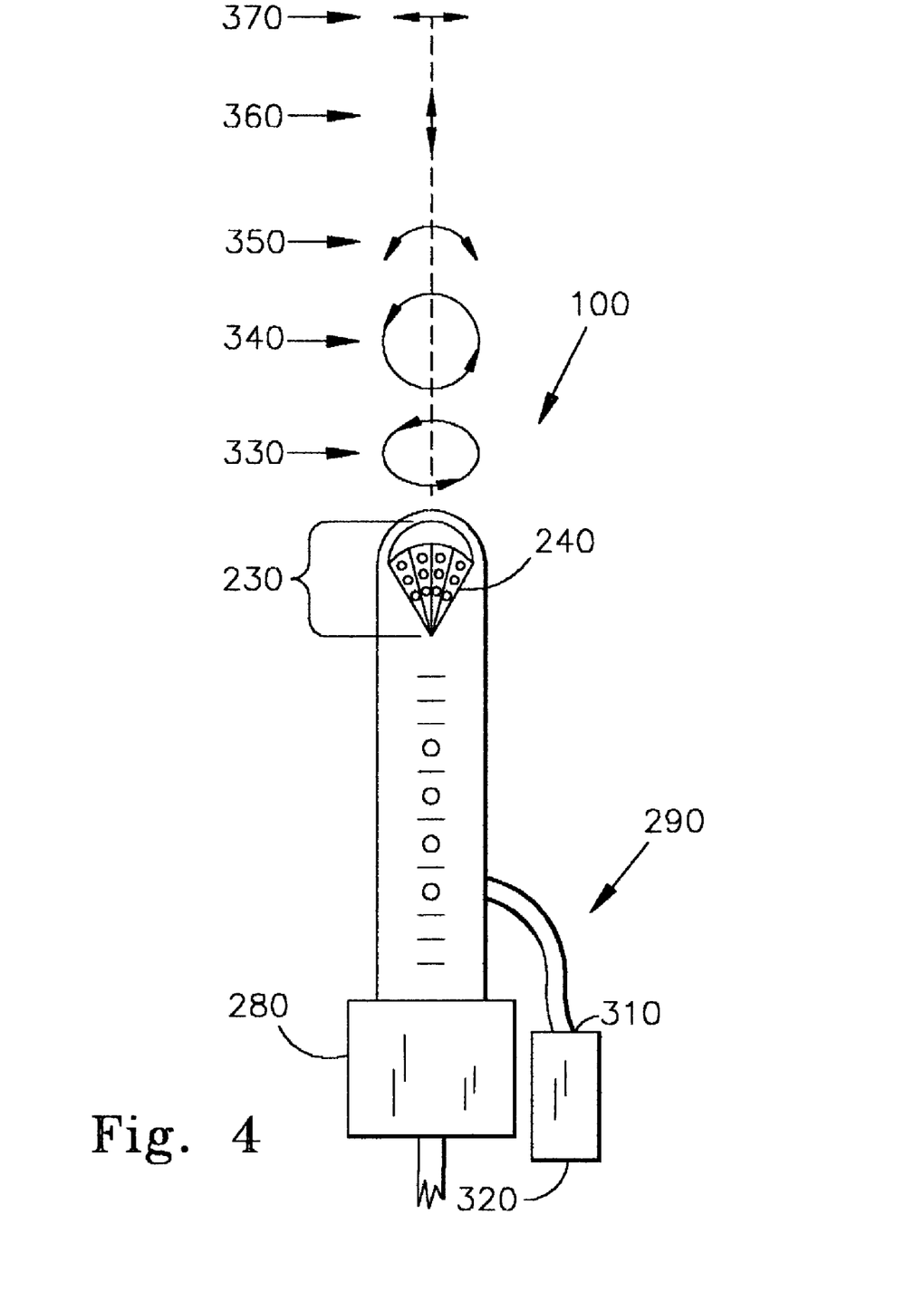
FIG. 4 shows a top view of the apparatus of FIG. 3.

FIG. 4 shows a top view of the apparatus 100 of FIG. 3. The generally pie-slice shaped perimeter of the base 240 of the burr 230 is more visible in FIG. 4. In the apparatus 100, the drive device 280 is automated to cause the elongated member 110 to move the base 240 in a generally elliptical pattern or mode as illustrated by the directional lines 330. In alternative embodiments, the drive device 280 may be automated to cause the elongated member 110 to move the base 240 in a generally circular mode, a generally arcuate mode, a generally longitudinal mode, or a generally transverse mode, as illustrated by the directional lines 340, the directional lines 350, the directional lines 360, and the directional lines 370, respectively, or automated to cause the elongated member 110 to move the base 240 in a random mode or any other suitable mode.

FIG. 5 shows a lateral cross-sectional view of the apparatus 100 of FIG. 3 prior to an exemplary removal of a posterior condylar osteophyte 380 from a knee joint. For removal of the posterior condylar osteophyte 380 with the apparatus 100, a surgeon or other operator makes incisions and/or otherwise creates a pathway to insert the second portion 170 of the elongated member 110 and the burr 230 into the patient's body so that the operator can abut the burr 230 against the osteophyte 380. This may include everting ("flipping aside") the patient's patella (not shown) or any other suitable procedures. It is noted that in the exemplary operations of FIG. 5, the operator needs to flex the knee joint merely to an angle of about 90 degrees. However, it should be appreciated that alternative embodiments of the present invention may be used to remove osteophytes from the hip, the elbow, or other areas, and the procedures to gain access to the osteophyte(s) may vary accordingly.

Continuing the example, with the driver device 280 and the suction device 320 deactivated or turned off, the operator inserts the second portion 170 of the elongated member 110 and the burr 230 into the patient's body and positions them such that the perforated, non-smooth portion 260 of the burr 230 is adjacent to and faces generally toward the osteophyte 380 and the smooth surface 180 (see FIG. 3) of the second portion 170 abuts a first surface 390 of the distal femur 400. The stop member 160 may be abutted against a second surface of the distal femur 400.

After this initial alignment of the apparatus 100, the operator activates or turns on the driver device 280 and the suction device 320 to cause the elongated member 110 to move the burr 230 and to cause suction through the perforated, non-smooth portion 260 of the burr 230, respectively. The smooth surface 180 (see FIG. 3) allows the elongated member 110 to slide on the first surface 390 of the distal femur 400 as it moves the burr 230.

Next, the operator pulls the apparatus 100 toward the outside of the patient's body (as indicated by the directional line 410) while maintaining the abutment of the smooth surface 180 (see FIG. 3) against the first surface 390 of the distal femur 400. As the burr 230 moves, the perforated, non-smooth portion 260 gradually scrapes or cuts away the osteophyte 380 and the suction device 320 sucks away the resulting bits or fragments of the osteophyte 380 through the perforated, non-smooth portion 260 and the passageway 200.

The operator continues pulling outward on the apparatus 100 until the osteophyte 380 has been removed. To this end, the operator may make a visual determination that the osteophyte 380 has been removed by observing the distal femur 400 with a naked eye or with the aid of a remote camera or other imaging device, or by inferring the position of the burr 230 from observation of the position of the graduations 150; the operator may make a tactile determination that the osteophyte 380 has been removed by alternately operating the apparatus 100 and reaching into the patient's body to feel the distal femur 400 with a finger; or the operator may in any other suitable manner determine that the osteophyte 380 has been removed. It is noted that suitable embodiments of the present invention may be coupled to a haptic arm, a robotic assembly, and/or computerized device, or the like, for an automatic determination that the osteophyte 380 has been removed. FIG. 6 shows a lateral cross-sectional view of the apparatus 100 of FIG. 3 after removal of the osteophyte 380 of FIG. 5.

Figure 7:
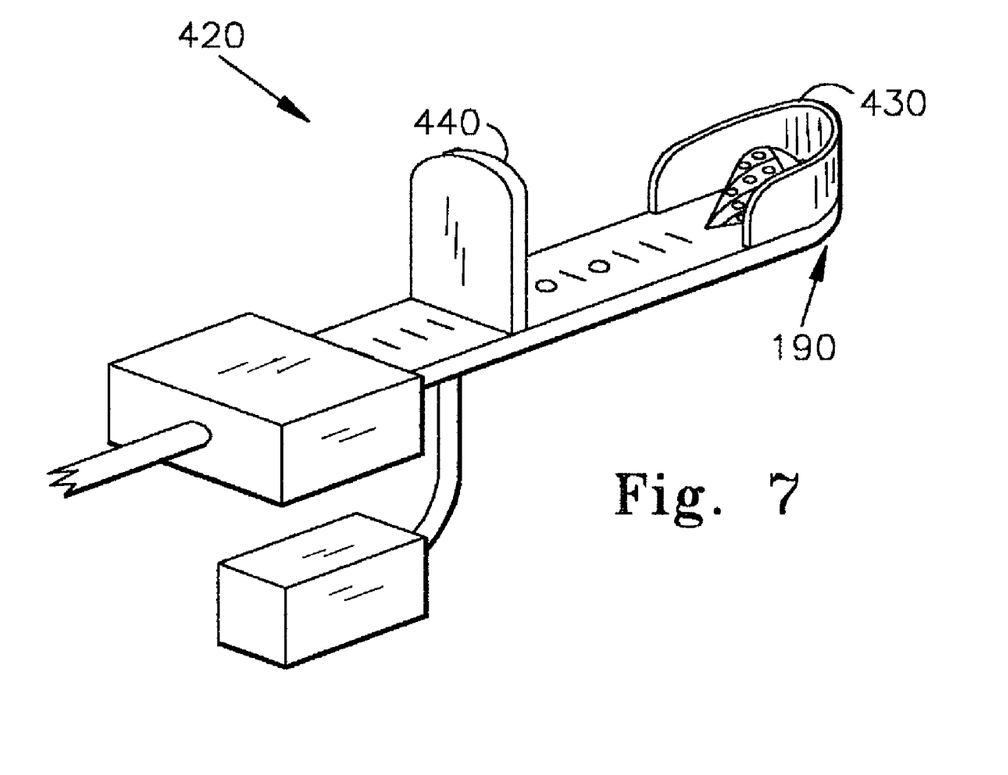
FIG. 7 shows a perspective view of an exemplary alternative apparatus for removing an osteophyte according to the present invention.

FIG. 7 shows a perspective view of an exemplary alternative apparatus for removing an osteophyte 420 according to the present invention. The alternative apparatus 420 is like the exemplary apparatus 100 (see FIG. 3) except for the addition of a blunt end wall 430 at the blunt end 190 and the incorporation of a wall into the alternative stop member 440. It should be appreciated that the end wall 430 may facilitate insertion and manipulation of the alternative apparatus 420.

Figure 8:
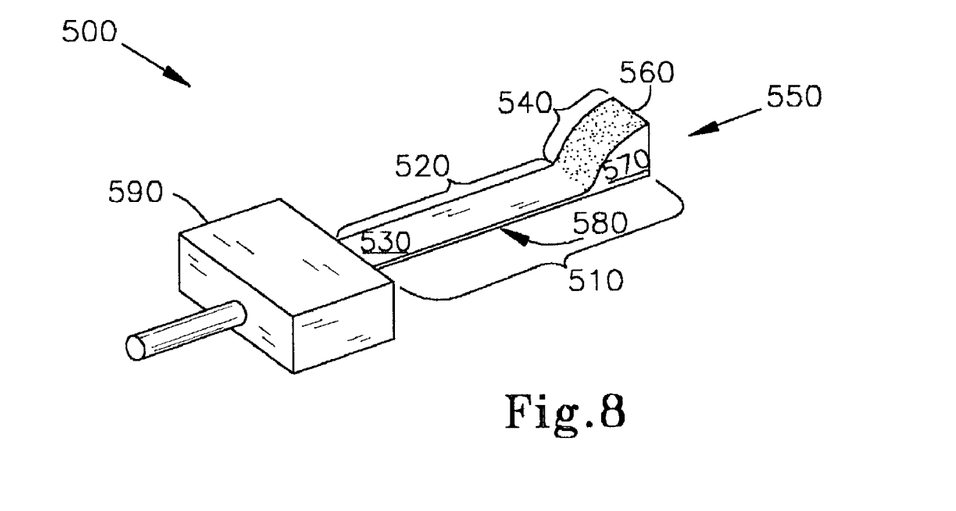
FIG. 8 shows a perspective view of another exemplary alternative apparatus for removing an osteophyte according to the present invention.

FIG. 8 shows a perspective view of another exemplary alternative apparatus for removing an osteophyte 500 according to the present invention. The apparatus 500 includes an elongated member 510 made from materials suitable for use in surgical procedures. In the apparatus 500, the elongated member 510 is reusable, and accordingly, is made suitable for sterilization in an autoclave. In alternative embodiments, the elongated member 510 may be disposable. The elongated member 510 includes a generally plank-shaped first portion 520. The first portion 520 includes a generally planar, smooth top surface 530. The elongated member 510 also includes a second portion 540. The second portion 540 includes a blunt end 550 and a non-smooth top surface 560. The non-smooth top surface 560 faces generally toward the first portion 520 and forms roughly half an arch (when viewed laterally) from the smooth top surface 530 to the blunt end 550. In the apparatus 500, the non-smooth top surface 560 includes diamond dust or fragments. In alternative embodiments, the non-smooth top surface 560 may include any other abrasives, serrations, studs, edges, or the like that are suitable for removing osteophytes. Further, the first portion 520 and the second portion 540 together form a generally planar, smooth bottom surface 580. The second portion 540 includes opposing sidewalls 570 (one of which is not visible in FIG. 8) that span between the non-smooth top surface 560 and the bottom surface 580. It is noted that in alternative embodiments the non-smooth top surface 560 may be perforated and the elongated member 510 may be configured to define a channel that is pneumatically coupled to the perforations such that a suction device may be added to carry away bits or fragments of an osteophyte during operation in a manner similar to that of the exemplary apparatus 100 (discussed above). Additionally, it should be appreciated that in alternative embodiments the elongated member 510 may be narrower, wider, may include additional curvatures, angles and/or contours, or may be configured in any other suitable manner.

A drive device 590 is attached to the first portion 520 of the elongated member 510. The drive device 590 is configured and operates in the same manner as the drive device 280 (discussed above). To this end, it should be appreciated that in the apparatus 500, the first portion 520 is suitably configured to attach to the drive device 590 in manner similar to that of an oscillating saw blade. Further, it should be readily appreciated that the exemplary apparatus 500 is operated in a similar manner to the exemplary apparatus 100 (discussed above).

Figure 9:
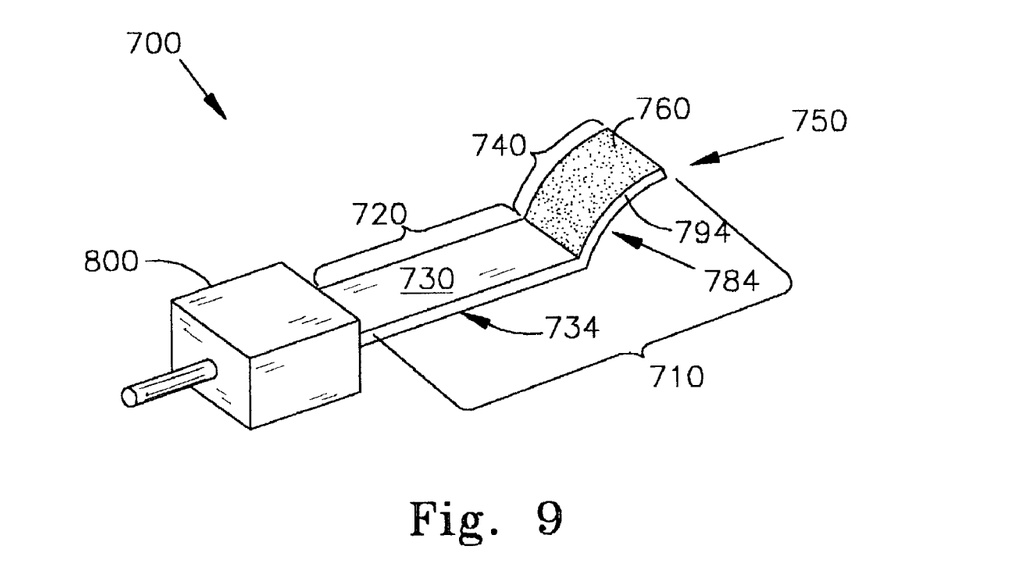
FIG. 9 shows a perspective view of another exemplary alternative apparatus for removing an osteophyte according to the present invention.

FIG. 9 shows a perspective view of another exemplary alternative apparatus for removing an osteophyte 700 according to the present invention. The apparatus 700 includes an elongated member 710 made from materials suitable for use in surgical procedures. In the apparatus 700, the elongated member 710 is reusable, and accordingly, is made suitable for sterilization in an autoclave. In alternative embodiments, the elongated member 710 may be disposable. The elongated member 710 includes a generally plank-shaped first portion 720. The first portion 720 includes a generally planar, smooth top surface 730 and a generally planar, smooth bottom surface 734. The elongated member 710 also includes a second portion 740. The second portion 740 includes a blunt end 750 and a non-smooth top surface 760. The non-smooth top surface 760 faces generally toward the first portion 720 and forms roughly half an arch (when viewed laterally) from the smooth top surface 730 to the blunt end 750. In the apparatus 700, the non-smooth top surface 760 includes diamond dust or fragments. In alternative embodiments, the non-smooth top surface 760 may include any other abrasives, serrations, studs, edges, or the like that are suitable for removing osteophytes. The second portion 740 also includes an arched, smooth bottom surface 784. The bottom surface 784 faces generally away from the first portion 720 and forms roughly half an arch (when viewed laterally) from the smooth bottom surface 734 to the blunt end 750. The second portion 740 includes opposing sidewalls 794 (one of which is not visible in FIG. 9) that span between the non-smooth top surface 760 and the smooth bottom surface 784. It is noted that in alternative embodiments the non-smooth top surface 760 may be perforated and the elongated member 710 may be configured to define a channel that is pneumatically coupled to the perforations such that a suction device may be added to carry away bits or fragments of an osteophyte during operation in a manner similar to that of the exemplary apparatus 100 (discussed above). Additionally, it should be appreciated that in alternative embodiments the elongated member 710 may be narrower, wider, may include additional curvatures, angles and/or contours, or may be configured in any other suitable manner.

A drive device 800 is attached to the first portion 720 of the elongated member 710. The drive device 800 is configured and operates in the same manner as the drive device 280 (discussed above). To this end, it should be appreciated that in the apparatus 700, the first portion 720 is suitably configured to attach to the drive device 800 in manner similar to that of an oscillating saw blade. Further, it should be readily appreciated that the exemplary apparatus 700 is operated in a similar manner to the exemplary apparatus 100 (discussed above).

Figure 10:
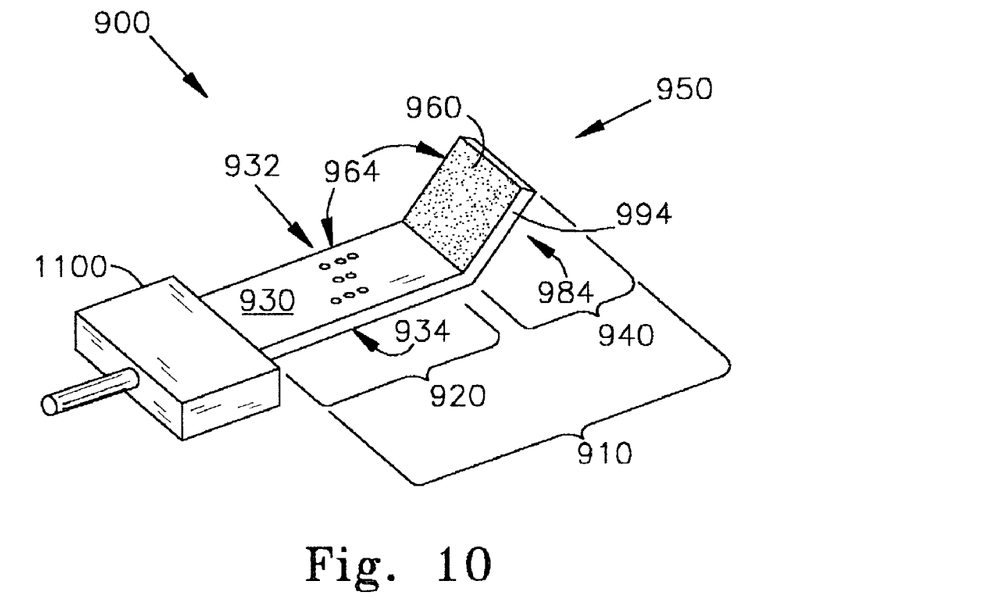
FIG. 10 shows a perspective view of another exemplary alternative apparatus for removing an osteophyte according to the present invention.

FIG. 10 shows a perspective view of another exemplary alternative apparatus for removing an osteophyte 900 according to the present invention. The apparatus 900 includes an elongated member 910 made from materials suitable for use in surgical procedures. In the apparatus 900, the elongated member 910 is reusable, and accordingly, is made suitable for sterilization in an autoclave. In alternative embodiments, the elongated member 910 may be disposable. The elongated member 910 includes a generally plank-shaped first portion 920. The first portion 920 includes a generally planar, smooth top surface 930 with a grid 932 of cylindrical holes, recesses, dots or other suitable reference markings. The first portion 920 also includes a generally planar, smooth bottom surface 934. The elongated member 910 further includes a generally plank-shaped second portion 940. The second portion 940 includes a blunt end 950 and a generally planar, non-smooth top surface 960. The non-smooth top surface 960 faces generally toward the first portion 920 and extends from the smooth top surface 930 to the blunt end 950 at an angle 964 of about 120 degrees relative to the plane of the smooth top surface 930. In the apparatus 900, the non-smooth top surface 960 includes diamond dust or fragments. In alternative embodiments, the non-smooth top surface 960 may include any other abrasives, serrations, studs, edges, or the like that are suitable for removing osteophytes. Further, it is noted that in alternative embodiments the angle 964 may be about 90 degrees, 135 degrees, or any other suitable angle. The second portion 940 also includes a smooth bottom surface 984 that faces generally away from the first portion 920. The second portion 940 includes opposing sidewalls 994 (one of which is not visible in FIG. 10) that span between the non-smooth top surface 960 and the smooth bottom surface 984. It is noted that in alternative embodiments the non-smooth top surface 960 may be perforated and the elongated member 910 may be configured to define a channel that is pneumatically coupled to the perforations such that a suction device may be added to carry away bits or fragments of an osteophyte during operation in a manner similar to that of the exemplary apparatus 100 (discussed above). Additionally, it should be appreciated that in alternative embodiments the elongated member 910 may be narrower, wider, may include additional curvatures, angles and/or contours, or may be configured in any other suitable manner.

A drive device 1100 is attached to the first portion 920 of the elongated member 910. The drive device 1100 is configured and operates in the same manner as the drive device 280 (discussed above). To this end, it should be appreciated that in the apparatus 900, the first portion 920 is suitably configured to attach to the drive device 1100 in manner similar to that of an oscillating saw blade. Further, it should be readily appreciated that the exemplary apparatus 900 is operated in a similar manner to the exemplary apparatus 100 (discussed above). The grid 932 is used to infer the position of the non-smooth top surface 960 in a similar manner to inferring the position of the burr 230 from the graduations 150 during operation f the exemplary apparatus 100.

Figure 11:
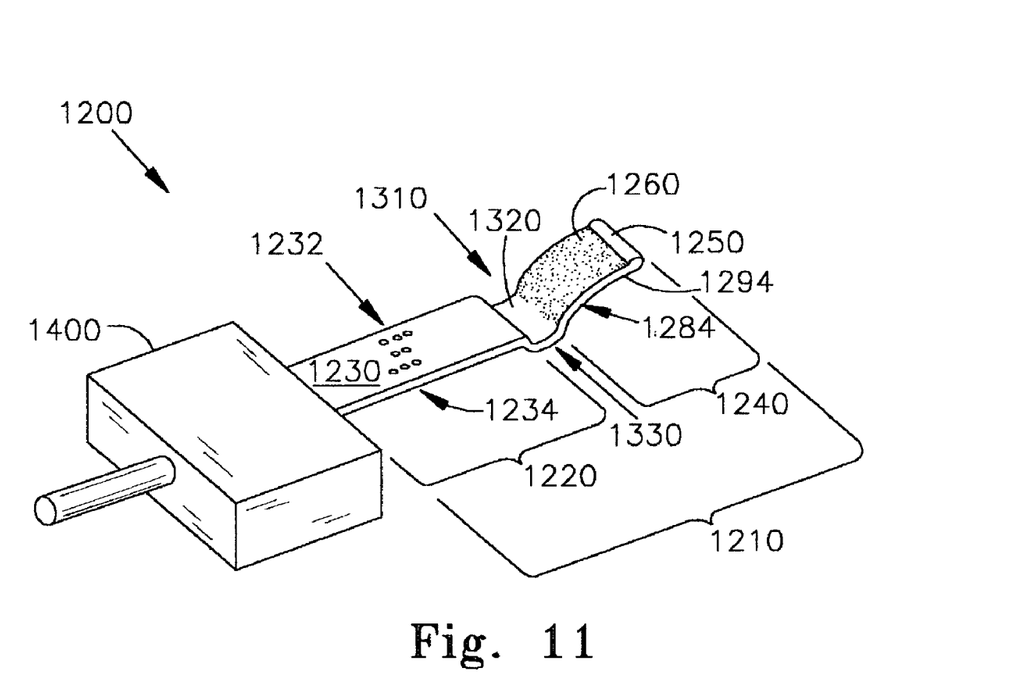
FIG. 11 shows a perspective view of another exemplary alternative apparatus for removing an osteophyte according to the present invention.

FIG. 11 shows a perspective view of another exemplary alternative apparatus for removing an osteophyte 1200 according to the present invention. The apparatus 1200 includes an elongated member 1210 made from materials suitable for use in surgical procedures. In the apparatus 1200, the elongated member 1210 is reusable, and accordingly, is made suitable for sterilization in an autoclave. In alternative embodiments, the elongated member 1210 may be disposable. The elongated member 1210 includes a generally plank-shaped first portion 1220. The first portion 1220 includes a generally planar, smooth top surface 1230 with a grid 1232 of cylindrical holes, recesses, dots or other suitable reference markings. The first portion 1220 also includes a generally planar, smooth bottom surface 1234. The elongated member 1210 also includes a second portion 1240. The second portion 1240 includes a curled or lipped blunt end 1250 and a non-smooth top surface 1260. The non-smooth top surface 1260 faces generally toward the first portion 1220 and forms roughly half an arch (when viewed laterally) from the plane of the smooth top surface 1230 to the blunt end 1250. In the apparatus 1200, the non-smooth top surface 1260 includes diamond dust or fragments. In alternative embodiments, the non-smooth top surface 1260 may include any other abrasives, serrations, studs, edges, or the like that are suitable for removing osteophytes. The second portion 1240 also includes an arched, smooth bottom surface 1284. The bottom surface 1284 generally faces away from the first portion 1220 and forms roughly half an arch (when viewed laterally) from the plane of the smooth bottom surface 1234 to the blunt end 1250. The second portion 1240 includes opposing sidewalls 1294 (one of which is not visible in FIG. 11) that span between the non-smooth top surface 1260 and the smooth bottom surface 1284. The elongated member 1210 also includes a third portion 1310 that forms a generally U-shaped transverse trough or depression between the first portion 1220 and the second portion 1240. The third portion 1310 includes a smooth top surface 1320 and a smooth bottom surface 1330. It is noted that in alternative embodiments the non-smooth top surface 1260 may be perforated and the elongated member 1210 may be configured to define a channel that is pneumatically coupled to the perforations such that a suction device may be added to carry away bits or fragments of an osteophyte during operation in a manner similar to that of the exemplary apparatus 100 (discussed above). Additionally, it should be appreciated that in alternative embodiments the elongated member 1210 may be narrower, wider, may include additional curvatures, angles and/or contours, or may be configured in any other suitable manner.

A drive device 1400 is attached to the first portion 1220 of the elongated member 1210. The drive device 1400 is configured and operates in the same manner as the drive device 280 (discussed above). To this end, it should be appreciated that in the apparatus 1200, the first portion 1220 is suitably configured to attach to the drive device 1400 in manner similar to that of an oscillating saw blade. Further, it should be readily appreciated that the exemplary apparatus 1200 is operated in a similar manner to the exemplary apparatus 100 (discussed above). The grid 1232 is used to infer the position of the non-smooth top surface 1260 in a similar manner to inferring the position of the burr 230 from the graduations 150 during operation f the exemplary apparatus 100.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. An apparatus for removing an osteophyte, the apparatus comprising:
   an elongated member including a generally planar smooth surface and a blunt end; and
   a burr including a generally convex non-smooth surface extending from the generally planar smooth surface of the elongated member at a location proximal to the blunt end, and further including a smooth surface facing generally toward the blunt end of the elongated member.

2. The apparatus of claim 1, wherein the generally convex non-smooth surface of the burr is perforated by a plurality of openings, the elongated member defines a passageway, and the burr is pneumatically coupled to the passageway.

3. The apparatus of claim 1, wherein the burr includes a base having a generally pie-slice shaped perimeter, and the generally convex non-smooth surface of the burr extends from at least a portion of the base.

4. The apparatus of claim 3, wherein the generally convex non-smooth surface of the burr is perforated by a plurality of openings, the elongated member defines a passageway, and the burr is pneumatically coupled to the passageway.

5. The apparatus of claim 1, wherein the elongated member is generally tongue-shaped.

6. The apparatus of claim 1, further comprising a wall coupled to the blunt end of the elongated member.

7. The apparatus of claim 1, further comprising a drive device coupled to the elongated member, the drive device being automated to cause the elongated member to move the burr.

8. The apparatus of claim 7, wherein the drive device is automated to cause the elongated member to move the burr in a generally elliptical mode.

9. The apparatus of claim 7, wherein the drive device is automated to cause the elongated member to move the burr in a generally circular mode.

10. The apparatus of claim 7, wherein the drive device is automated to cause the elongated member to move the burr in a generally arcuate mode.

11. The apparatus of claim 7, wherein the drive device is automated to cause the elongated member to move the burr in a generally longitudinal mode.

12. The apparatus of claim 7, wherein the drive device is automated to cause the elongated member to move the burr in a generally transverse mode.

13. The apparatus of claim 7, further comprising a suction device coupled to the elongated member.

14. The apparatus of claim 7, further comprising a suction device coupled to the burr.

15. The apparatus of claim 14, wherein the burr includes a surface perforated by a plurality of openings.

16. An apparatus for removing an osteophyte from a bone in a patient's body, the bone including a first surface and a second surface, the apparatus comprising:
a means for removing the osteophyte from the bone; and
a means, coupled to the removing means, for positioning the removing means relative to at least the first surface of the bone;
wherein the positioning means includes a generally planar surface and further includes a means for limiting the position of the removing means relative to at least the second surface of the bone, and the removing means includes a non-smooth surface extending at least one of arcuately and angularly relative to the generally planar surface.

17. The apparatus of claim 16, further comprising a means, coupled to the removing means, for automatically moving the removing means.

18. The apparatus of claim 17, wherein the moving means includes a means for moving the removing means in a generally elliptical mode.

19. The apparatus of claim 17, further comprising a means, coupled to the removing means, for suctioning at least a portion of the osteophyte from the patient's body.

20. An apparatus for removing an osteophyte, the apparatus comprising:
an elongated member including a first portion and a second portion, the first portion including a generally planar smooth top surface, the second portion including a blunt end and further including a non-smooth top surface extending from the blunt end at least one of arcuately and angularly towards the generally planar smooth top surface; and
a drive device coupled to the elongated member, the drive device being automated to cause the elongated member to move the non-smooth top surface.

21. The apparatus of claim 20, wherein the drive device is automated to cause the elongated member to move the non-smooth top surface in one of a generally elliptical mode, a generally circular mode, a generally arcuate mode, a generally longitudinal mode, and a generally transverse mode.

22. The apparatus of claim 20, further comprising:
a suction device coupled to the elongated member;
wherein the non-smooth top surface is perforated.

23. The apparatus of claim 20, wherein the non-smooth top surface arches from the smooth top surface to the blunt end.

24. The apparatus of claim 23, wherein the non-smooth top surface forms roughly half an arch.

25. The apparatus of claim 24, wherein the second portion further includes a smooth bottom surface facing generally away from the first portion and forming roughly half an arch.

26. The apparatus of claim 25, wherein the elongated member further includes a third portion forming a generally U-shaped transverse trough between the first portion and the second portion.

27. The apparatus of claim 20, wherein the non-smooth top surface is generally planar.

28. The apparatus of claim 27, wherein the second portion is generally plank-shaped.

29. The apparatus of claim 28, wherein the non-smooth top surface extends from the smooth top surface to the blunt end at an angle relative to the plane of the smooth top surface of at least 90 degrees and less than 120 degrees.

30. The apparatus of claim 28, wherein the non-smooth top surface extends from the smooth top surface to the blunt end at an angle relative to the plane of the smooth top surface of at least 120 degrees and less than 135 degrees.

31. The apparatus of claim 28, wherein the non-smooth top surface extends from the smooth top surface to the blunt end at an angle relative to the plane of the smooth top surface of about 120 degrees.

32. The apparatus of claim 28, wherein the non-smooth top surface extends from the smooth top surface to the blunt end at an angle relative to the plane of the smooth top surface of at least 135 degrees and less than 180 degrees.

33. An apparatus for removing an osteophyte from a bone including a first surface and a second surface, the apparatus comprising:
an elongated member including a generally planar smooth surface and a blunt end; and
a burr including a generally convex non-smooth surface extending from the generally planar smooth surface of the elongated member at a location proximal to the blunt end, and further including a smooth surface facing generally toward the blunt end of the elongated member;
wherein the generally planar smooth surface of the elongated member is positioned to guide against the first surface of the bone and the generally convex non-smooth surface of the burr is positioned to rasp the second surface of the bone.

34. The apparatus of claim 33, wherein the generally convex non-smooth surface of the burr is perforated by a plurality of openings, the elongated member defines a passageway, and the burr is pneumatically coupled to the passageway.

35. The apparatus of claim 33, wherein the burr includes a base having a generally pie-slice shaped perimeter, and the generally convex non-smooth surface of the burr extends from at least a portion of the base.

36. The apparatus of claim 35, wherein the burr includes a smooth portion facing generally toward the blunt end of the elongated member.

37. The apparatus of claim 36, wherein the generally convex non-smooth surface of the burr is perforated by a plurality of openings, the elongated member defines a passageway, and the burr is pneumatically coupled to the passageway.

38. The apparatus of claim 33, wherein the elongated member is generally tongue-shaped.

39. The apparatus of claim 33, further comprising a wall coupled to the blunt end of the elongated member.

40. The apparatus of claim 33, further comprising a drive device coupled to the elongated member, the drive device being automated to cause the elongated member to move the burr.

41. The apparatus of claim 40, wherein the drive device is automated to cause the elongated member to move the burr in a generally elliptical mode.

42. The apparatus of claim 40, wherein the drive device is automated to cause the elongated member to move the burr in a generally circular mode.

43. The apparatus of claim 40, wherein the drive device is automated to cause the elongated member to move the burr in a generally arcuate mode.

44. The apparatus of claim 40, wherein the drive device is automated to cause the elongated member to move the burr in a generally longitudinal mode.

45. The apparatus of claim 40, wherein the drive device is automated to cause the elongated member to move the burr in a generally transverse mode.

46. The apparatus of claim 40, further comprising a suction device coupled to the elongated member.

47. The apparatus of claim 40, further comprising a suction device coupled to the burr.

48. The apparatus of claim 47, wherein the burr includes a surface perforated by a plurality of openings.

49. An apparatus for removing an osteophyte from a bone in a patient's body, the bone including a first surface, a second surface, and a third surface, the apparatus comprising:

a means for removing the osteophyte from the first surface of the bone;

a means, coupled to the removing means, for positioning the removing means relative to at least the second surface of the bone; and a means, coupled to the positioning means, for limiting a position of the removing means relative to at least the third surface of the bone.

50. The apparatus of claim 49, wherein the positioning means includes a generally planar surface, the removing means includes a non-smooth surface extending at least one of arcuately and angularly relative to the generally planar surface, and the non-smooth surface is positioned to rasp at least the first surface of the bone.

51. The apparatus of claim 50, further comprising a means, coupled to the removing means, for automatically moving the removing means.

52. The apparatus of claim 51, wherein the moving means includes a means for moving the removing means in a generally elliptical mode.

53. The apparatus of claim 51, further comprising a means, coupled to the removing means, for suctioning at least a portion of the osteophyte from the patient's body.

* * * * *